United States Patent [19]
Hunt et al.

[11] Patent Number: 4,580,036
[45] Date of Patent: Apr. 1, 1986

[54] GAS CHROMATOGRAPHY OVEN

[75] Inventors: Richard J. Hunt; Joseph H. F. Wadsworth; Frank V. Hubbard, all of Cambridge, England

[73] Assignee: U.S. Philips Corporation, New York, N.Y.

[21] Appl. No.: 620,783

[22] Filed: Jun. 14, 1984

[30] Foreign Application Priority Data

Jun. 15, 1983 [GB] United Kingdom ................ 8316267

[51] Int. Cl.⁴ ............................................. F27D 11/00
[52] U.S. Cl. ........................................ 219/400; 55/197
[58] Field of Search .................... 219/400; 55/67, 197, 55/386; 73/23.1; 422/70, 89; 210/656; 126/190

[56] References Cited

U.S. PATENT DOCUMENTS 4,181,613  1/1980  Welsh ..................................... 55/197

FOREIGN PATENT DOCUMENTS 2921358  12/1980  Fed. Rep. of Germany ........ 55/197

82/01661  5/1982  PCT Int'l Appl. ................... 55/386

Primary Examiner—C. L. Albritton
Assistant Examiner—Teresa J. Walberg
Attorney, Agent, or Firm—Paul R. Miller

[57] ABSTRACT

In a gas chromatography oven, the heated enclosure is designed to be of a low thermal mass to permit more rapid programmed temperature changes, and to provide good oven cooling for work on the columns between analyses. Easy access to the columns is desirable, and accordingly, the present invention provides a heating enclosure having a door and at least one chromatograph column supported on a wall of the enclosure with the wall being transverse to the door opening and with the wall being movable from a first position having the column in the enclosure to a second position having the column outside of the enclosure. In such a structure, access to the column can be made outside of the enclosure so that the enclosure itself can be made smaller and of lower thermal mass.

22 Claims, 11 Drawing Figures

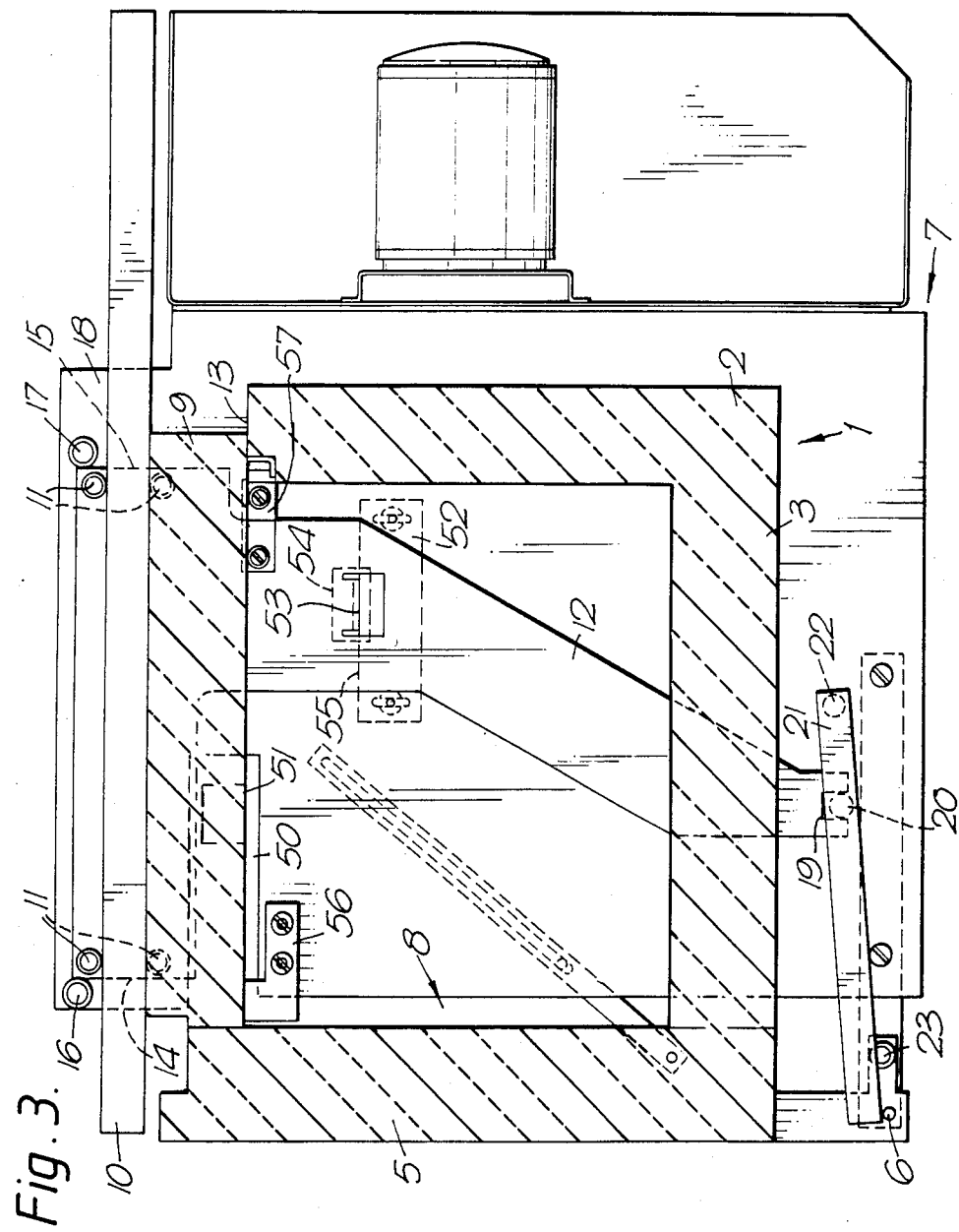

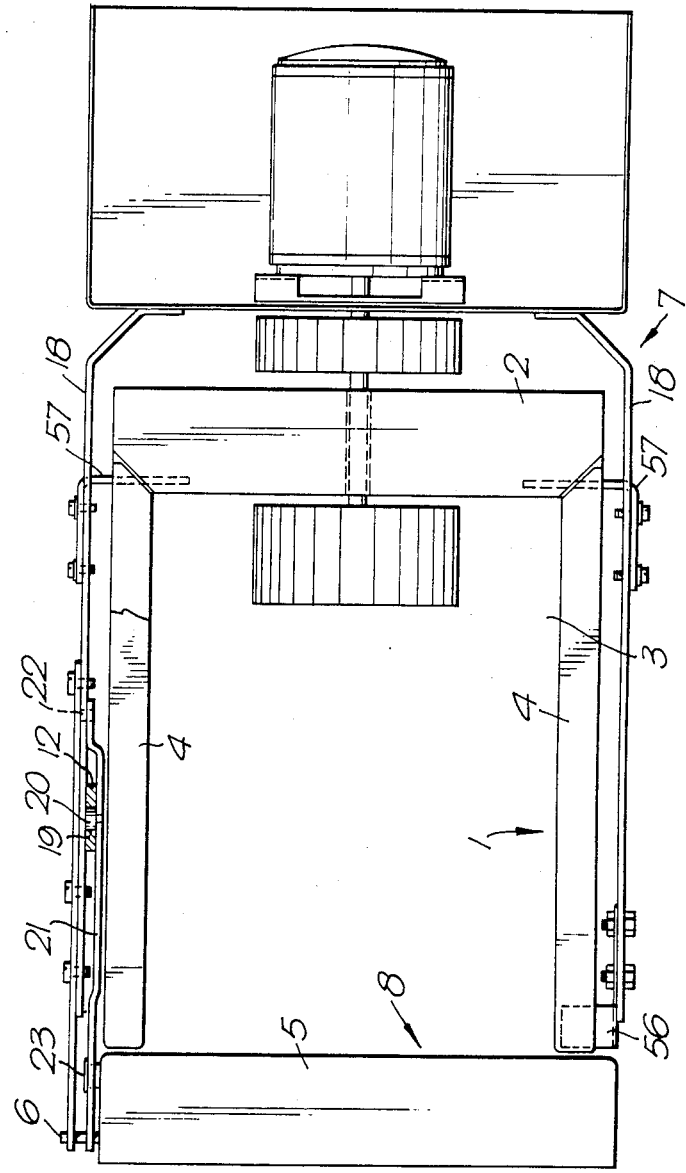

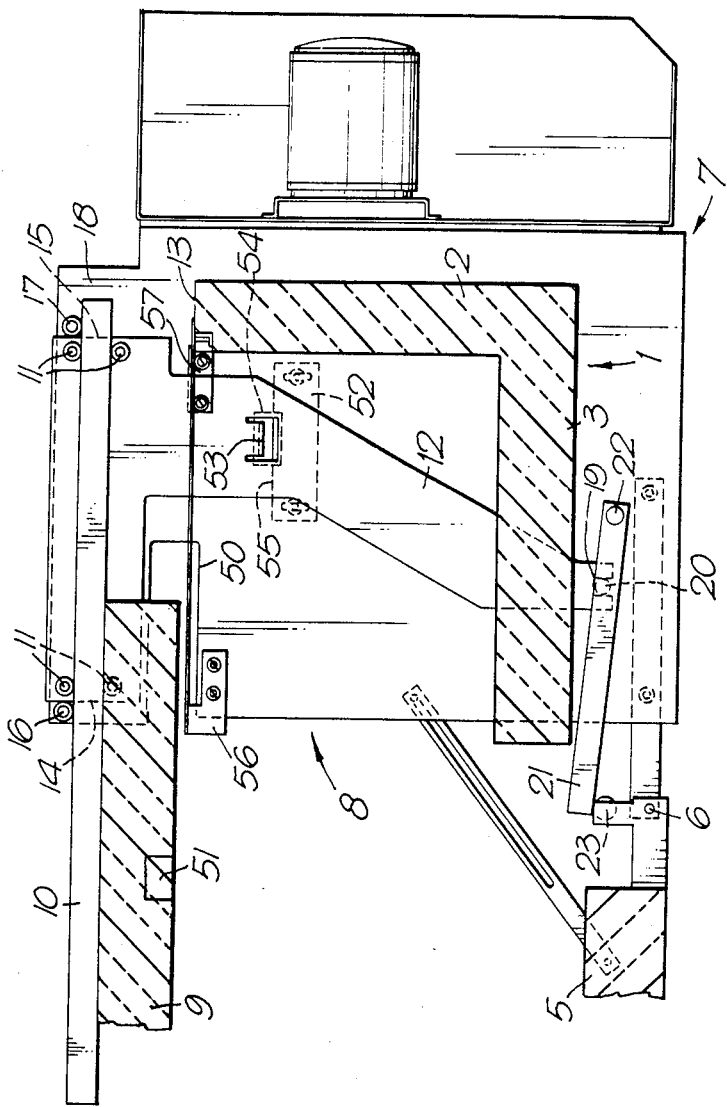

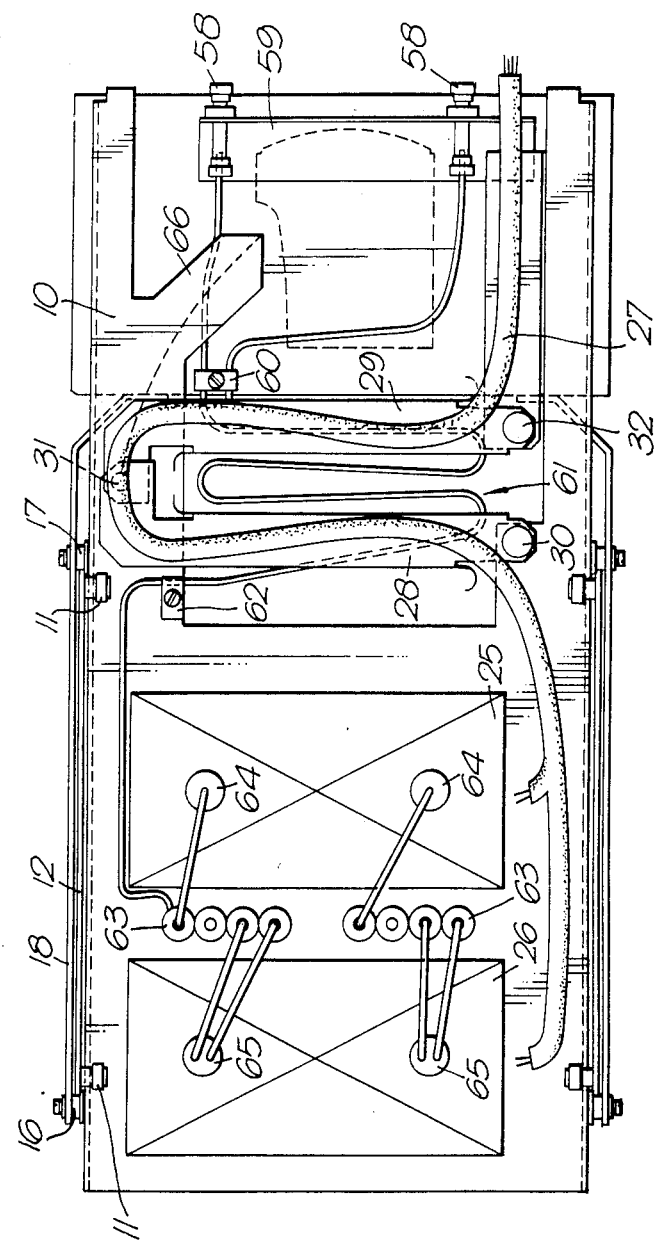

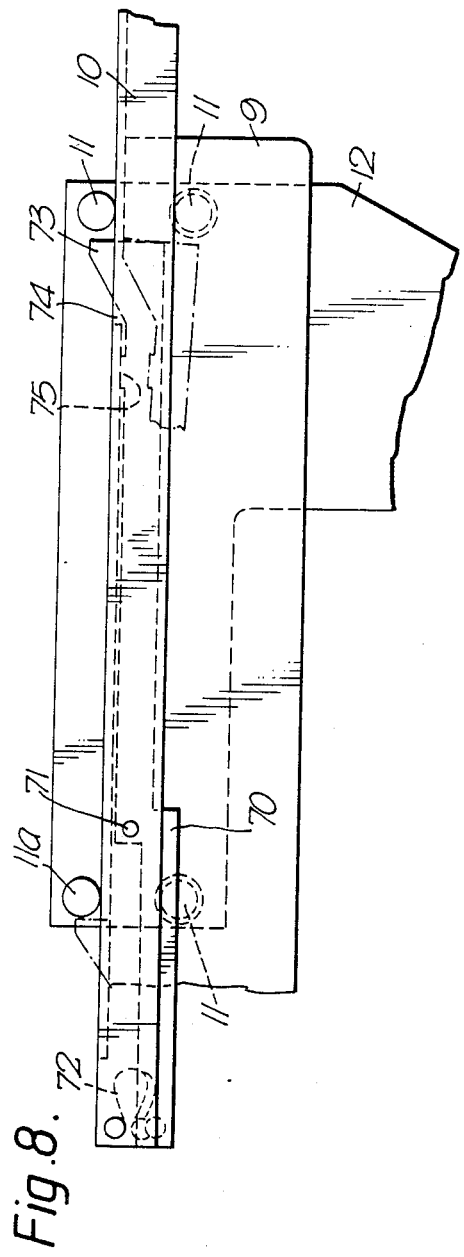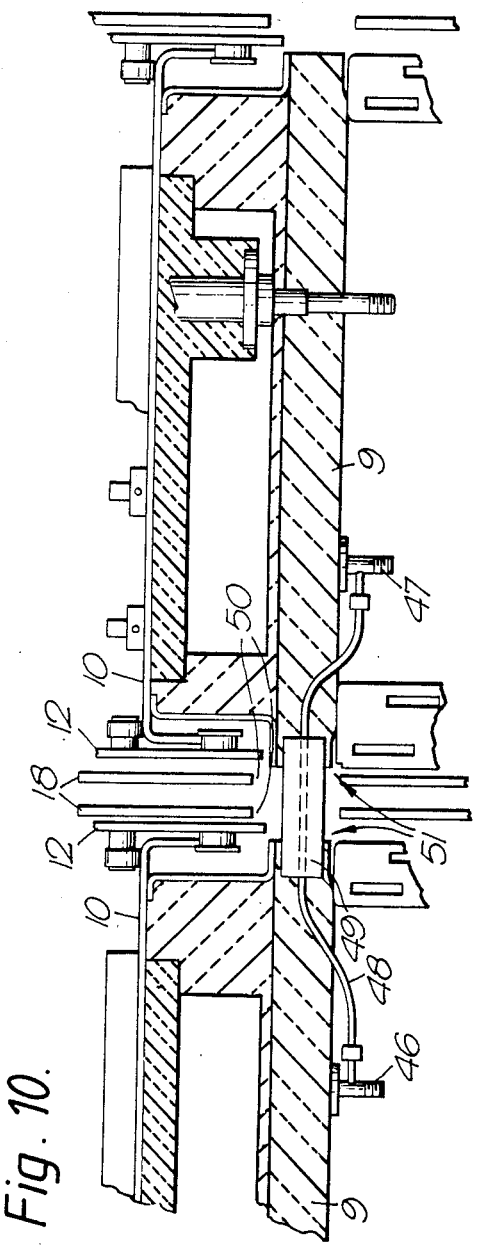

GAS CHROMATOGRAPHY OVEN

This invention relates to a gas chromatograph oven comprising a heatable enclosure having a door, one or more chromatograph columns supported in a predetermined position relative to a wall of the enclosure, and means for passing a carrier gas and sample through the columns.

Gas chromatographs generally use an electrically heated enclosure, or oven, in which the separating column or columns are maintained at a controlled temperature. Additional ovens, which control the temperature of the column injection zone and/or the detector, may be provided adjacent to or within the column oven. The columns fitted between the injection port and the detector have a wide variety of lengths, diameters and stationary phases. The chromatographic analysis may involve programmed temperature control in which the temperature of the oven is varied in a predetermined manner. Consequently an oven of low thermal mass is desirable. Also, column switching may be employed in which the carrier gas and eluted components leaving the column are switched at a desired stage of separation from one column to another to enhance a particular separation. From the foregoing it will be clear that there is a distinct advantage in providing the analyst with as much access as possible to the columns and the associated pipework connections. Commonly, in prior art ovens hand access around the columns within the oven is provided through a front opening door. Consequently, access to the rearmost connections and pipework is difficult and only feasible when the oven has cooled down, slowing the rate at which analyses can be performed. In PCT patent application No. PCT/FI81/00079, Publication No. WO 82/01661, a gas chromatograph oven is described in which the columns are attached to the oven door which forms the top surface of the oven and which can be hinged upwards and backwards about a rear hinge to draw the columns up out of the oven. Work on the columns must take place over the top of the oven, possibly while hot, and access to the pipework when the door is raised is difficult as it is only accessible from the rear of the raised door.

It is an object of the invention to provide a gas chromatography oven having easy access to the chromatograph columns and associated pipework connections. It is another object of the invention to enable the provision of easy access to service connections which pass through a wall of the oven to the chromatograph columns.

The invention provides a gas chromatograph oven as set forth in the opening paragraph, characterised in that the wall extends in a direction which is transverse to the door opening and in that, when the door is open, the wall is movable from a first position in which the columns are within the enclosure to a second position in which the columns are outside the enclosure with the wall being supported by the oven in the second position and extending in the same direction in the first and second positions. The wall may be slidable between the positions. Herein, by slidable is meant that at least a part of the wall or of a body connected to the wall slides or rolls over a surface. In the first position, the wall closes an aperture in the enclosure and the boundaries of this aperture may define a plane. In this case the wall is planar and the transverse direction is parallel to the plane of the aperture. Depending on the degree of thermal seal required between the slidable wall and the fixed walls of the oven the friction between these walls as the slidable wall is withdrawn may vary and in some instances become unacceptably large. An embodiment in which this friction in minimised is characterised in that a mechanism is provided coupling the door to the wall so that the opening movement of the door separates the wall from the enclosure. The enclosure may be suspended within a supporting structure and the mechanism may comprise side members on either side of the enclosure and adjacent opposite edges of the movable wall parallel to the sliding motion with sliding guides mounted on said members and engaging the edges, and a linkage connecting the opening movement of the door with movement of the side members, relative to the supporting structure, in a direction normal to the movable wall to separate the movable wall from the enclosure.

The enclosure may be a rectangular box, the door being hinged along the bottom horizontal edge of the opening. In this case the slidable wall is the top horizontal wall of the box and slides forward over the door when open. Access to chromatograph columns attached to the underside of the slidable wall is then possible from three sides. Pipework connections on top of the horizontal slidable wall are freely available. Drawn forward away from the oven heated volume the columns and pipework are able to cool down more rapidly and heat from the remainder of the oven is largely avoided.

Embodiments of the invention will now be described, by way of example, with reference to the accompanying drawings in which:

FIG. 1 shows a schematic elevation view of a gas chromatograph oven in accordance with the invention, FIG. 2 shows the oven of FIG. 1 with the oven top and chromatograph column drawn forward out of the oven, FIGS. 3 and 5 show elevation views and FIG. 4 a plan view of a second gas chromatograph oven in accordance with the invention, FIG. 6 shows a top plan view of flexible service conduits for the chromatograph columns of the second oven, FIG. 7 shows an electric heater and air circulation system within the oven of FIG. 6, FIG. 8 shows a locking mechanism for the oven top.

FIG. 10 shows the interconnection of the columns of two ovens when placed side-by-side.

Figure 1:
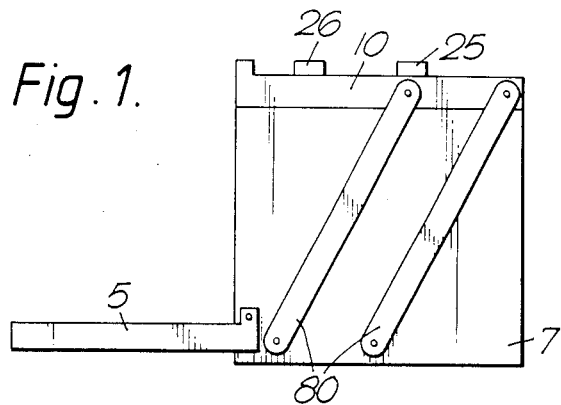
Figure 2:
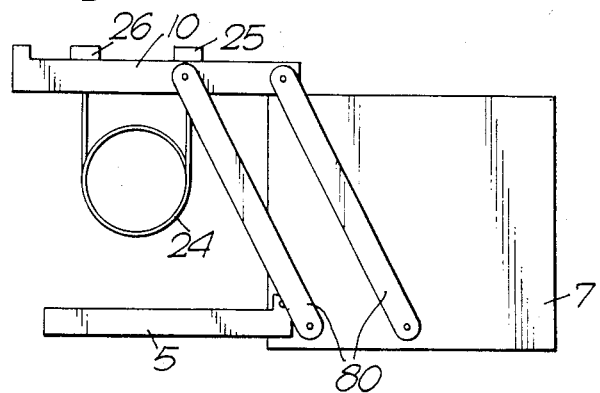

Referring to FIGS. 1 and 2, an oven supporting structure 7 is shown within which a thermally insulated heatable oven enclosure (not shown) is supported. The enclosure is open at the top and front. An oven door 5 is shown in the lowered position. The open front of oven enclosure is flush with the front of the supporting structure. When the door 5 is raised it seals the oven enclosure and covers the front edge of a carriage 10. A thermally insulated top wall (not shown) of the oven is carried within carriage 10, its lower surface being flush with the bottom of carriage 10. The top wall is transverse to the door opening.

In a first position of the carriage shown in FIG. 1, the carriage rests on the top of the side walls of the supporting structure 7. The open top of the enclosure is flush with the side wall tops so that in this first position the top wall carried by carriage 10 seals the top of the oven enclosure.

The carriage 10 is attached to the supporting structure via two parallel arms 80 of equal length, on each side of the oven supporting structure, pivoted at their lower ends on the side walls and at their upper ends on the carriage. When the carriage 10 is drawn forward, the arms 80 lift the carriage and oven top away from the supporting structure and oven enclosure respectively thereby reducing friction and wear.

In FIG. 2, the carriage 10 has been drawn fully forward into a second position in which the underside of the oven top is almost entirely clear of the oven enclosure. FIG. 2 also shows a chromatograph column 24 attached to the movable oven top via an injection port 25 and a detector port 26 which provide means for passing a carrier gas and sample through the column. Thus, when the door is open, the top wall is movable from a first position in which the column is within the enclosure to a second position in which the column is outside the enclosure.

Alternative mechanisms are possible for drawing the carriage and oven top horizontally out of the oven enclosure in a substantially straight line parallel to the carriage while at the same time lifting the oven top clear of the enclosure side walls to avoid friction.

In a first alternative the arctuate path is provided by slot cams or tracks on the supporting structure, one each for the four rollers projecting from the carriage. The slot cams can be shaped to provide an initial lift of the carriage as the carriage is drawn forward and optionally, a final drop at the limit of forward travel of the carriage as a means of holding the carriage in the forward position while work is carried out on the columns.

Figure 11:
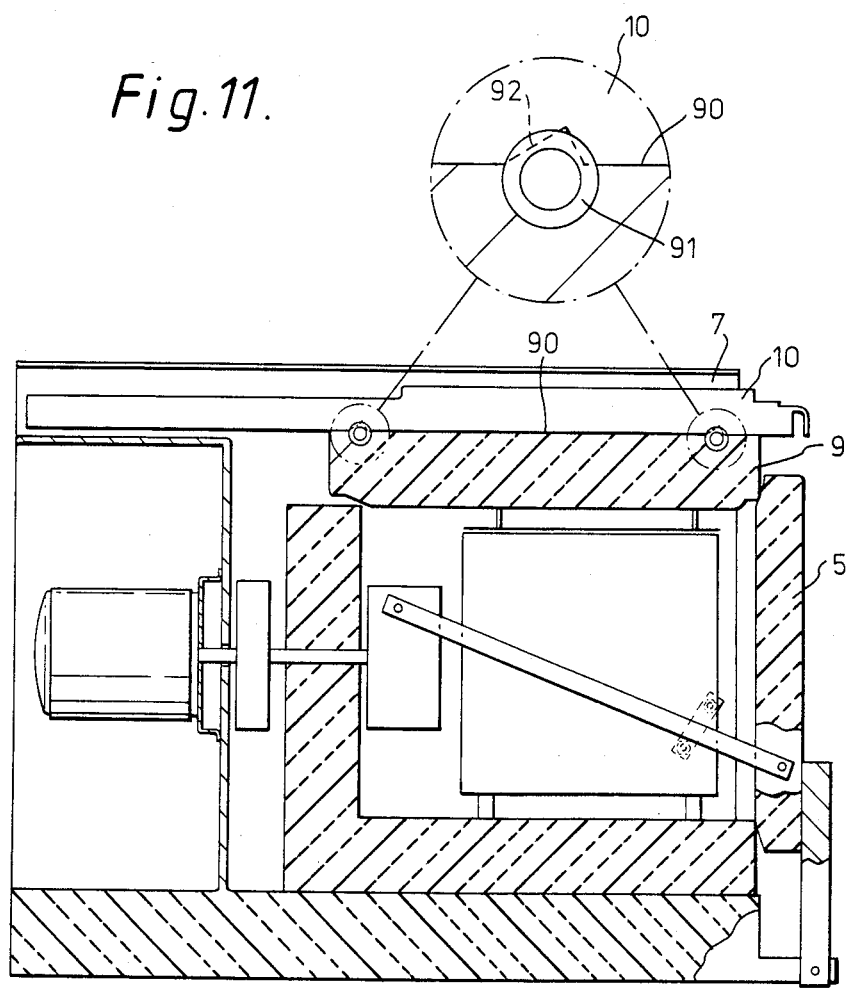
FIG. 11 shows another embodiment in accordance with the invention.

FIG. 11 shows a variant of this first alternative in which two tracks 90 are provided, one on each side of the carriage 10, each track running on two rollers 91 on its side of the carriage, the rollers being free to rotate about their fixing points on the side supporting structure 7. One side of the oven is shown in FIG. 11 with the other side supporting structure to which the rollers are attached removed for clarity. Each track is provided with two Vee-shaped notches 92 at the same spacing as the rollers 91. In the closed oven position shown in FIG. 11 the notches engage with the rollers, lowering the carriage 10 and with it an oven top 9 into contact with the top of oven walls. When the door is opened and the carriage pulled forward, the sloping parts of the notches ride up rollers 91, lifting the oven top clear of the oven walls before it is drawn forward on the rollers.

In a second alternative, a pair of separated horizontal parallel bar handles are mechanically linked to the four carriage rollers so that, when the handles are pressed together by hand, the rollers are driven downward relative to the carriage thereby lifting the carriage prior to forward motion. The handle pressing may also be coupled to a mechanical lock, releasing the carriage for forward motion.

A third alternative will now be described in relation to the remaining FIGS. 3 to 10 inclusive.

Referring to FIGS. 3, 4 and 5, the oven enclosure 1 is a rectangular box having thermally insulated floor, rear, and side walls 3,2,4 respectively supported within an outer supporting structure 7. Side walls 4 are not shown in FIGS. 3 and 5 so that further details of the assembly can be more clearly seen. The front opening 8 of the oven is closed by a door 5 hinged about a horizontal axis 6, the closed position being shown in both FIGS. 3 and 4. The top of the oven is closed by a thermally insulated slidable wall or oven top 9, not shown in FIG. 4 to enable further details of the oven to be more clearly illustrated. The oven top 9 is attached to the underside of a carriage 10 which extends sideways beyond the walls 4. Carriage 10 is supported from the underside and guided by rollers 11 attached in pairs to the inside of two vertically movable side members 12, one either side of the oven. With the side members 12 lifted into an upper position as shown in FIG. 3, rollers 11 engage the underside of carriage 10 to lift oven top 9 clear of the upper surface 13 of the rear and side walls of the oven. Carriage 10 and oven top 9 can then be drawn out manually, moving horizontally between the rollers 11. In FIG. 4 a lower section of the lifting mechanism is shown on only one side of the oven for clarity.

The side members 12 have straight, parallel, vertical edges 14 and 15 which are guided between rollers 16 and 17 respectively attached to the outer side walls 18 of the supporting structure 7. The lower end of each side member has a vertical slot 19 engaging with a pin 20 on a side lever 21 pivoted at one end about a stub axle 22 attached to the outer side wall 18. The free ends of side levers 21 each rest upon a roller 23 attached to the inside of door 5 at a point rearward of axis 6 when the door is in the closed position shown in FIG. 3. With door 5 in the closed position, lever 21 is lowered sufficiently to allow the oven top 9 to rest on the upper surface 13 of the side and rear walls of the oven with the pin 20 lowered clear of the upper end of slot 19. When the door is opened as shown in FIG. 5, roller 23 first lifts lever 21 sufficiently to move pin 20 into contact with the upper end of slot 19. Thereafter continuing opening movement of the door lifts each lever 21, each side member 12 and, via rollers 11, the carriage 10 and oven top 9. The full door opening movement lifts oven top 9 into an upper position allowing free horizontal sliding motion of oven top 9 out over the open door 5.

In FIGS. 3 and 5 the lifting side members 12 are flat plates approximating in shape to a "7". The portion of each member 12 extending between the upper part having rollers 11 and the lower part having slot 19 is located towards the rear of the oven so that the forward part of oven top 9 is accessible from the side through corresponding slots 50 in the supporting walls 18. An oven interconnection zone 51 is then available to allow two such ovens to be placed side-by-side and a crosscoupling to be made between chromatograph columns in the two ovens.

The insulating material on the underside of oven top 9 is elastically compressible to a limited extent to ensure a good thermal seal between oven top 9 and the rear and side walls 2 and 4 respectively. However, as will be described later, the oven top 9 and carriage 10 will carry relatively heavy injection and detection apparatus together with ovens for this apparatus. To avoid crushing the compressible material, the downward travel of the side members 12 is limited by a pair of stop plates 52 adjustably attached, one each, to the outside of supporting walls 18. A ledge 53 on each member 12 projects outward through an aperture 54 in wall 18 to engage with the upper edge 55 of stop plate 52, setting the lower limit to its travel and bearing the weight of oven top 9.

FIG. 4 shows the upper surface of the rear wall 2, one side wall 4 and a part of the other side wall 4. A section of the lifting mechanism for wall 9, at the level of lever 21, is shown on only one side of the oven, the lifting mechanism on the other side of the oven being omitted for clarity. The oven walls are supported by means of front brackets 56 (only one shown) welded to the upper surface of walls 4 and bolted to the walls 18. Rear brackets 57, bolted to walls 18, extend under the upper edge of side walls 4 and rear wall 2, these walls resting freely on the brackets to allow rearward movement of the oven due to expansion on heating.

Figure 7:
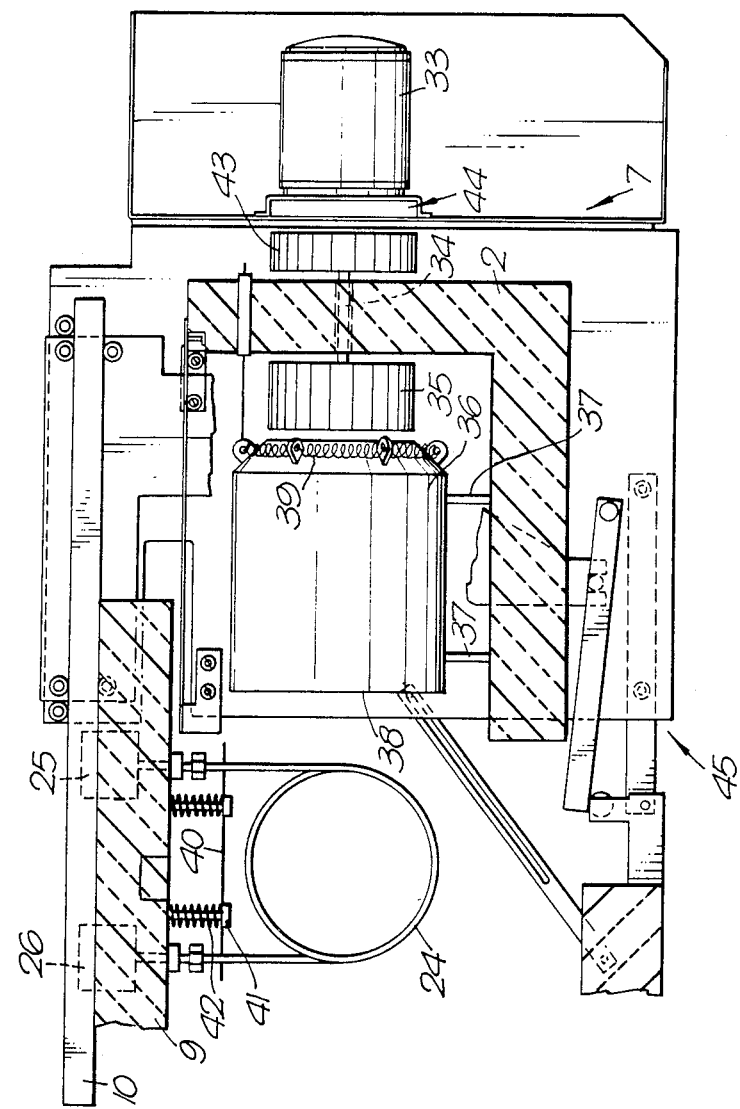

In FIG. 7 a coiled chromatograph column is shown at 24. One end of the column is attached to an injection zone oven 25 and the other end is attached to a detector oven 26. Both ovens are electrically heated and recessed within the oven top 9 and carriage 10. Oven 25 is used to control the temperature of the injection zone to ensure correct vaporization of the liquid sample injected by hypodermic needle via a silicone rubber plug, not shown, in the top of the injection zone from the topside of oven top 9. Oven 26 is used to control the temperature of the detector when a flame detector is used and condensation of the products of combustion or of the column eluent must be avoided. The plane of the coiled column is vertical and parallel to the direction of sliding motion of oven top 9, easing movement of the coil past obstacles in the oven.

The oven is heated by an electrical resistive heating element. The heating element and means for ensuring uniform temperature throughout the oven are also shown in FIG. 7. A fan motor 33 is mounted outside the rear wall 2 of the oven, a shaft 34 from the motor passing horizontally through wall 2. A fan 35 of the centrifugal impeller type is mounted on shaft 34 adjacent one end of an open-ended tubular baffle 36 attached to and spaced apart from the oven walls by pillars 37. The action of fan 35 is to draw air rearwards through the baffle and to discharge it radially into the annular space between the baffle and wall, along which space it passes to re-enter the open front 38. The electrical heating element 39 is mounted outside the baffle 36 which therefore shields the columns 24, arranged inside the baffle, from direct radiation from the heating element. The radially discharged air from the fan is heated before it enters the annular space and hence has time to mix and equalise in temperature before re-entering the baffle to heat the columns 24. The control of temperature is achieved using a platinum resistance thermometer (not shown) either inside or outside the baffle to control the power to the heating element, via suitable electronic control means, to servo the oven temperature to a preset value. A plate 40 which forms part of the baffle is mounted on the underside of oven top 9, the column ends passing through it. Plate 40 is held at a predetermined separation from top 9 by headed pins 41 and springs 42. With top 9 lifted into its upper position as shown in FIG. 7, plate 40 is lifted clear of the top of the baffle and is free to slide out with top 9. When door 5 is closed and wall 9 lowered onto the oven top 13, plate 40 is lowered into contact with the side walls of baffle 36. Springs 42 are compressed slightly holding plate 40 in contact with the baffle to complete its tubular form.

A second impeller fan 43 is mounted on motor shaft 34 between the rear oven wall 2 and the rear wall of the supporting structure 7. Vents (not shown) are provided at 44 near the fan axis and at 45 below the front of the oven. These vents can be opened and closed under remote control so that, as required, cool air can be drawn in and driven between the oven walls and the outer supporting structure. Rapid cool down between samples can therefore be obtained. Also the vents can be opened during a sample run as a means of obtaining reductions of oven temperature which may be part of a programme of temperature changes required during the run.

Service connections must be made to both ends of the column. At the injection zone a carrier gas, for example nitrogen at a pressure of about 2 bar, must be supplied to carry the vaporized sample through the column. One type of detector that may be used is a flame ionisation detector and for such a detector a supply of fuel gas and oxygen or air are required. The fuel gas is added to the carrier gas as it emerges from the column with the separated components of the sample. The mixture is burnt as a gas flame with the oxygen. The resulting ionised gases give rise to an electrical output signal in known manner. Thus, each column may require connection to at least three gas supplies.

FIG. 6 shows how these connections can be made by flexible service conduits. In the oven illustrated two columns 24 are provided. The gases are brought to each column by narrow bore flexible metal tubes.

The external connections for the gases are made to eight connectors 58, only two of which are shown, provided on a bracket 59 at the rear of the oven. The tubes are gathered together at a clamp 60 attached to the top of the oven supporting structure. The tubes are bent into a zig-zag pattern 61 and gathered together at a clamp 62 attached to the carriage 10. The length of tubing in the zig-zag pattern is sufficient to allow substantially free motion of carriage 10 out to the limit of its forward travel with tube flexing kept well within its elastic limit. The tubes are connected, one each, to right angle connectors 63 in a row between the injector oven 25 and the detector oven 26. From the right angle connectors connections are then made to the injectors 64 and the detectors 65.

All the electrical service connections are gathered together into a single flexible sleeve 27 resting freely in channels along the top of L-shaped arms 28 and 29. Arm 28 is pivoted at one end to the top of carriage 10 about a vertical axis 30. Arm 29 is pivoted at one end to the top of the oven supporting structure about a vertical axis 32. The other ends of arms 28 and 29 are pivoted together about a vertical axis 31, permitting scissor-like motion of arms 28 and 29 as carriage 10 is drawn forward away from the oven. A support plate 66, part of the carriage 10, prevents pivot 31 and arms 28 and 29 sagging and touching the gas tubes. Thus the columns can be drawn out of the oven without being disconnected from their services.

One advantage of this oven construction is that the columns can be withdrawn from the oven for changing without waiting for the oven to cool down and yet with much reduced risk of burns to the operator's hand or arms. Full access is provided to the link between column and detector which is especially important when capillary columns are to be connected to the detector. A consequence of obtaining access to the columns external to the oven is that the oven itself can be made smaller. Several advantages follow from this. First, the heating power is reduced. Second, the amount of thermal insulation is reduced which can be used either to lower the oven cost or to employ better quality insulating materials and so further reduce heating power. Third, the reduced thermal mass allows more rapid changes of temperature to be obtained for the same accuracy of temperature setting, which is of benefit with temperature programming. Finally, faster oven cooling is obtained.

A benefit with this sliding top wall arrangement, the injection port being on the sliding wall, is that the height of the oven is kept convenient for manual sample injection. This is because provision does not have to be made at the bottom of the oven for space to enable the columns to be threaded upward through the wall insulation when making connections to the injector and detector. A further benefit is that the mode of injection is vertical which is especially suited to automatic injectors.

When the oven top 9 and carriage 10 have been withdrawn from above the oven enclosure, the carriage must be locked in the 'out' position so that mechanical work on the connections can be carried out easily. FIG. 8 shows the carriage locking mechanism. A cranked lever 70 is pivoted about horizontal axis 71 on each side of carriage 10. The front of each lever 70 is spring loaded downwards by spring 72 in compression between the carriage and the lever. The rear of lever 70 is provided with a sawtooth 73 which, under the action of spring 72, normally projects above the carriage through a slot 74. A stop 75 on the lever bears against the underside of the carriage top to define the vertical position of the lever. Near the limit of forward travel of the carriage the sloping surface of sawtooth 73 bears on forward roller 11a, depressing the lever against spring force which finally drives the vertical edge of the sawtooth up in front of roller 11a, locking the carriage in the forward position. The carriage is released by manually compressing spring 72 between a pair of parallel bar handles on the carriage and levers, withdrawing the sawtooth below the carriage top and clear of roller 11a.

Mention has been made above of the advantage of being able to switch the carrier gas and eluted components leaving a column at a desired stage of separation to another column which is possibly at a different temperature to the first column. Desirably, therefore, it should be possible to stand two or more ovens side-by-side and connect the output of a column in one oven to the input of a column in an adjacent oven.

FIG. 10 shows a section of the tops of two ovens placed side-by-side. The oven interconnection zones 51 of the ovens are exposed via the slots 50 in the walls 18. The output 46 of a column in one oven is coupled to the input 47 of a column in the other oven via an interconnection pipe 48. An interconnection oven 49 is provided to maintain pipe 48 at a temperature which will prevent undesired condensation of the sample components as they pass between the ovens.

Figure 9:
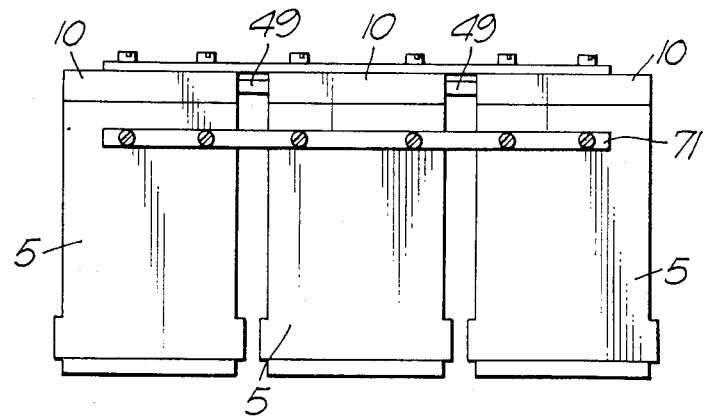
FIG. 9 shows three ovens side-by-side with the doors and tops coupled together.

When two or more ovens are stood side-by-side and have columns interconnected for simultaneous use, it is necessary to avoid damage to the interconnections when the doors 5 are opened and the carriages 10 are drawn forward. FIG. 9 shows how mechanical connections are made between the doors 5 and the carriages 10. Firstly, the doors 5 are connected by a single rigid bar member 71 fixed along the tops of all the doors. All the doors now open together and the lift of the side members 12 in all ovens occurs together, avoiding any differences in level of the interconnection zones. Second, the carriages are rigidly linked together by a bar member 72 so that all the carriages are drawn forward together, avoiding any displacement between the interconnection zones.

We claim:

1. A gas chromatograph oven comprising a heatable enclosure having a door, at least one chromatograph column supported in a predetermined position relative to a wall of said enclosure, and means for passing a carrier gas and sample through said column, characterised in that said wall extends in a direction which is transverse to an opening in said enclosure closed by said door, in that, when said door is open, said wall is movable from a first position in which said column is within said enclosure to a second position in which said column is outside said enclosure, said wall being supported by the oven in said second position and extending in the same direction in said first and second positions, characterised in that said wall is slidable between said positions, and characterised in that a mechanism is provided coupling the door to said wall so that opening said door separates said wall from said enclosure to allow free sliding motion of said wall.

2. An oven as claimed in claim 1, characterised in that said enclosure is suspended within a supporting structure, and in that said mechanism comprises side members on either side of said enclosure and adjacent opposite edges of the movable wall parallel to said sliding motion, sliding guides mounted on said members and engaging said edges, and a linkage connecting said opening of said door with movement of said side members, relative to the supporting structure, in a direction normal to said movable wall to separate said movable wall from said enclosure.

3. An oven as claimed in claim 1 or claim 2, characterised in that said enclosure is a rectangular box, in that said door is hinged along a bottom horizontal edge of said opening, and in that the slidable wall is a top horizontal wall of said enclosure and is slidable forward over said door when open.

4. An oven as claimed in claim 1 or claim 2, characterised in that service connections are made to said column through said wall, and in that said service connections are linked to the outside of the oven by flexible conduits which permit the motion of the wall.

5. An oven as claimed claim 1 or claim 2, characterised in that said column to be heated lies mostly within a tubular baffle within said enclosure and spaced apart from walls of said enclosure, in that a first open end of said baffle faces said door and the other end of said baffle is closed by a fan adapted to draw air from around said column and circulate it by the space between said baffle and said walls to said first open end, and in that part of said baffle facing said wall carrying said column permits movement of said column with said wall away from remainder portions of said baffle.

6. An oven as claimed in claim 5, wherein a heat source for heating said enclosure is mounted outside said baffle in said circulated air.

7. An assembly of at least two ovens as claimed in claim 1 or claim 2, the ovens being placed side-by-side, characterised in that access is provided to the side of each movable wall in all positions of said wall from said first to said second position so that a column of one oven can be connected to a column of an adjacent oven, carriages and doors of all said ovens of the assembly being linked for simultaneous movement.

8. A gas chromatograph oven comprising a heatable enclosure having a door, at least one chromatograph column supported in a predetermined position relative to a wall of said enclosure, and means for passing a carrier gas and sample through said column, characterised in that said wall extends in a direction which is transverse to an opening in said enclosure closed by said door, in that, when said door is open, said wall is movable from a first position in which said column is within said enclosure to a second position in which said column is outside said enclosure, said wall being supported by the oven in said second position and extending in the same direction in said first and second positions, characterised in that projections on the movable wall engage with tracks on said enclosure shaped to provide an initial lift of said wall clear of said enclosure as it is drawn away from said first position.

9. An oven as claimed in claim 8, characterised in that said wall is slidable between said positions.

10. A gas chromatograph oven comprising a heatable enclosure having a door, at least one chromatograph column supported in a predetermined position relative to a wall of said enclosure, and means for passing a carrier gas and sample through said column, characterised in that said wall extends in a direction which is transverse to an opening in said enclosure closed by said door, in that, when said door is open, said wall is movable from a first position in which said column is within said enclosure to a second position in which said column is outside said enclosure, said wall being supported by the oven in said second position and extending in the same direction in said first and second positions, characterised in that the movable wall is provided with tracks engaging with rollers in fixed positions on a supporting structure for said heatable enclosure, and in that said tracks have notches which engage with said rollers to lower said movable wall into contact with said enclosure when the oven is closed.

11. An oven as claimed in claim 10, characterised in that said wall is slidable between said positions.

12. In a gas chromatograph oven comprising a heatable enclosure having a door, at least one chromatograph column supported in a predetermined position relative to one wall of said enclosure, and means for passing a carrier gas and sample through said column, the improvement comprising said column being attached to said wall, said wall being movable transverse to an opening of said enclosure, said opening being closed by said door, said wall and said column being movable from a first position with said column inside said enclosure to a second position with said column outside said enclosure when said door is open, said wall being supported by said enclosure in said second position, and said wall extending in the same direction in said first and second positions.

13. An oven according to claim 12, wherein said wall is slidable between said first and second positions.

14. An oven according to claim 13, wherein a mechanism is provided to couple said door and said wall, said mechanism providing separation of said wall from said enclosure upon opening said door, said wall then being freely sliding.

15. An oven according to claim 14, wherein said enclosure is suspended within a supporting structure, and wherein said mechanism comprises side members on either side of said enclosure, said side members being adjacent opposite edges of said wall parallel to sliding motion of said wall; sliding guides mounted on said side members and engaging said edges; and a linkage connecting said door with said side members, relative to said supporting structure, to obtain movement of said wall in a direction normal to said enclosure to separate said wall and said enclosure.

16. An oven according to claim 14 or claim 15, wherein said enclosure is a rectangular box, wherein said door is hinged along a bottom horizontal edge of said opening, and wherein said wall is a top horizontal wall of said enclosure, said wall being slidable forward over said door upon opening.

17. An oven according to claim 12 or claim 13, wherein service connections are made to said column through said wall, said service connections being linked by flexible conduits to outside of the oven.

18. An oven according to claim 12 or claim 13, wherein said column lies mostly within a tubular baffle within said enclosure, said baffle being spaced from walls of said enclosure, wherein a first open end of said baffle faces said door, and a second end of said baffle is closed by a fan drawing air from around said column and circulating it between said baffle and said enclosure to said first open end, and wherein a part of said baffle facing said wall permits movement of said column with said wall away from said baffle.

19. An oven according to claim 18, wherein a heat source for heating said enclosure is mounted outside said baffle in said circulated air.

20. An oven according to claim 12 or claim 13, wherein projections on said wall engage tracks on said enclosure shaped to provide an initial lift of said wall from said enclosure.

21. An oven according to claim 12 or claim 13, wherein said wall is provided with tracks engaging rollers in fixed positions on a supporting structure for said enclosure, and wherein said tracks have notches engaging said rollers to lower said wall into contact with said enclosure.

22. An assembly of at least two ovens according to claim 12 or claim 13, wherein said ovens are placed side-by-side, wherein access is provided at sides of each said wall from said first position to said second position, a column of one of said ovens being connected to a column of an adjacent oven, and wherein said wall and said door of each of said ovens are linked for simultaneous movement.

* * * * *

UNITED STATES PATENT AND TRADEMARK OFFICE
CERTIFICATE OF CORRECTION

PATENT NO. : 4,580,036
DATED : April 1, 1986
INVENTOR(S) : RICHARD J. HUNT ET AL It is certified that error appears in the above-identified patent and that said Letters Patent is hereby corrected as shown below:

IN THE CLAIMS:

Claim 5, line 1, after "claimed" insert --in--.

Signed and Sealed this

Tenth Day of February, 1987

Attest:

DONALD J. QUIGG

Attesting Officer

Commissioner of Patents and Trademarks